United States Patent
Gregorich (10) Patent No.: US 7,479,158 B2
(45) Date of Patent: Jan. 20, 2009

(54) STENT WITH NESTED FLEXIBLE CONNECTORS FOR FLEXIBILITY AND CRIMPABILITY

(75) Inventor: Daniel Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 813 days.

(21) Appl. No.: 10/783,650

(22) Filed: Feb. 20, 2004

(65) Prior Publication Data

US 2005/0187606 A1    Aug. 25, 2005

(51) Int. Cl.
A61F 2/06    (2006.01)
(52) U.S. Cl. .................................................... 623/1.16
(58) Field of Classification Search ................ 623/1.15, 623/1.16, 1.11–1.14
See application file for complete search history.

(56) References Cited

U.S. PATENT DOCUMENTS

| | | | |
|---|---|---|---|
| 5,449,373 A | 9/1995 | Pinchasik et al. ........... 606/198 |
| 5,755,770 A | 5/1998 | Ravenscroft .................... 623/1 |
| 5,824,046 A | 10/1998 | Smith et al. ..................... 623/1 |
| 5,938,682 A | 8/1999 | Hojeibane et al. ........... 606/198 |
| 5,957,930 A | 9/1999 | Vrba ........................... 606/108 |
| 5,972,018 A | 10/1999 | Israel et al. .................. 606/198 |
| 6,017,363 A | 1/2000 | Hojeibane ...................... 623/1 |
| 6,033,433 A | 3/2000 | Ehr et al. ........................ 623/1 |
| 6,042,597 A | 3/2000 | Kveen et al. ................ 606/198 |
| 6,113,628 A | 9/2000 | Borghi ..................... 623/1.016 |
| 6,120,522 A | 9/2000 | Vrba et al. ................... 606/190 |
| 6,123,712 A | 9/2000 | Di Caprio et al. ........... 606/108 |
| 6,190,403 B1 | 2/2001 | Fischell et al. ................. 623/1 |
| 6,231,598 B1 | 5/2001 | Berry et al. ................. 623/1.15 |
| 6,261,319 B1 | 7/2001 | Kveen et al. ................ 623/1.15 |
| 6,290,720 B1 | 9/2001 | Khosravi et al. ............ 623/1.13 |
| 6,312,460 B2 | 11/2001 | Drasler et al. .............. 623/1.15 |
| 6,325,820 B1 | 12/2001 | Khosravi et al. ............ 623/1.13 |
| 6,325,821 B1 | 12/2001 | Gaschino et al. ........... 623/1.15 |
| 6,334,870 B1 | 1/2002 | Ehr et al. .................... 623/1.16 |
| 6,355,059 B1 | 3/2002 | Richter et al. .............. 623/1.17 |
| 6,398,806 B1 * | 6/2002 | You .......................... 623/1.15 |
| 6,451,049 B2 | 9/2002 | Vallana et al. ............. 623/1.15 |
| 6,478,816 B1 | 11/2002 | Kveen et al. ............... 623/1.15 |
| 6,485,509 B2 | 11/2002 | Killion et al. .............. 623/1.15 |
| 6,488,703 B1 | 12/2002 | Kveen et al. ............... 623/1.15 |

(Continued)

FOREIGN PATENT DOCUMENTS

WO    WO 02/32347    4/2002

OTHER PUBLICATIONS

U.S. Appl. No. 60/238,178, filed Oct. 5, 2000, DiCaprio et al.

*Primary Examiner*—Julian W Woo
*Assistant Examiner*—Victor X Nguyen
(74) *Attorney, Agent, or Firm*—Vidas, Arrett & Steinkraus (57) ABSTRACT

A stent comprises two serpentine bands, at least one first connector; and at least one second connector. The first and second connectors connect the two serpentine bands together. The first connector and the second each have at least a first portion of a first curvature and a second portion of a second curvature. The second portion being more flexible than the first portion. The first and second connectors are adjacent one another and the first portion of the first connector nests within the second portion of the second connector and the second portion of the second connector nests within the first portion of the first connector.

13 Claims, 4 Drawing Sheets

U.S. PATENT DOCUMENTS

| | | |
|---|---|---|
| 6,506,211 B1 | 1/2003 | Skubitz et al. .............. 623/1.15 |
| 6,562,067 B2 | 5/2003 | Mathis ...................... 623/1.16 |
| 6,623,240 B2 | 9/2003 | Ertl et al. ................... 415/163 |
| 6,669,723 B2 | 12/2003 | Killion et al. ............... 623/1.15 |
| 6,945,993 B2 * | 9/2005 | Kveen et al. ................ 623/1.15 |
| 2006/0025849 A1 * | 2/2006 | Kaplan et al. .............. 623/1.15 |

* cited by examiner

STENT WITH NESTED FLEXIBLE CONNECTORS FOR FLEXIBILITY AND CRIMPABILITY

BACKGROUND OF THE INVENTION

The use of stents in bodily lumen is well known. A stent is typically delivered in an unexpanded state to a desired location in a bodily lumen and then expanded. The stent may be expanded via the use of mechanical device such as a balloon or the stent may be self-expanding.

Because a stent often must be delivered through tortuous anatomy, it is desirable for the stent to be flexible and to have a low profile. In order to provide a low profile the stent is often crimped onto a balloon or catheter before entering a bodily lumen. In general, however, as a stent is crimped in order to minimize its profile, the likelihood of overlapping portions of the stent increases.

There remains a need for a stent having a low crimped profile without overlapping portions of the stent.

All US patents and applications and all other published documents mentioned anywhere in this application are incorporated herein by reference in their entirety.

Without limiting the scope of the invention in any way, the invention is briefly summarized in some of its aspects below. Additional details of the invention and/or additional embodiments of the invention may be found in the Detailed Description of the Invention below.

A brief abstract of the technical disclosure in the specification is provided as well for the purposes of complying with 37 C.F.R. 1.72.

SUMMARY OF THE INVENTION

In at least one embodiment, the invention is directed to a stent comprising two serpentine bands, at least one first connector, and, in some embodiments, at least one second connector. The first and second connectors may connect the two serpentine bands together. In some embodiments the first connector and the second connector may each have at least a first portion of a first curvature and a second portion of a second curvature. In at least some embodiments the second portion may be more flexible than the first portion. In some embodiments, the first and second connectors may be adjacent one another and the second portion of the first connector may nest within the first portion of the second connector and the second portion of the second connector may nest within the first portion of the first connector.

In some embodiments, a plurality of the first connectors and a plurality of the second connectors may be arranged in pairs. In some embodiments, each pair has a second portion of one first connector which may nest within a first portion of one second connector and a second portion of one second connector which may nest within a first portion of one first connector.

In some embodiments, the stent of this invention may comprise a plurality of serpentine bands wherein adjacent serpentine bands may be connected by a plurality of the first connector and a plurality of the second connector. In some embodiments, the first and second connectors which are circumferentially adjacent one another may be arranged in pairs wherein in each pair the second portion of one first connector may nest within the first portion of one second connector and the second portion of one second connector may nest within the first portion of one first connector.

In some embodiments each first connector may include at least one linear section connecting the first and second portions of the second connector and each second connector may include at least one linear section connecting the first and second portions of the second connector.

In some embodiments the second connector may have a shape which corresponds substantially to that of the first connector, rotated by 180 degrees.

In some embodiments the stent of this invention may be crimped about a catheter.

In some embodiments of the stent of this invention the curvature of the first portion of the first connector may be identical to the curvature of the first portion of the second connector and the curvature of the second portion of the first connector may be identical to the curvature of the second portion of the second connector.

In some embodiments of the stent of this invention the curvature of the first portion of the first connector may differ from the curvature of the first portion of the second connector and the curvature of the second portion of the first connector may differ from the curvature of the second portion of the second connector.

In some embodiments of the stent of this invention the first portion of the first connector may have a greater width than the second portion of the first connector and the first portion of the second connector may have a greater width than the second portion of the second connector.

In some embodiments of the stent of this invention the first portion of the first connector may have a greater thickness than the second portion of the first connector and the first portion of the second connector may have a greater thickness than the second portion of the second connector.

In some embodiments of the stent of this invention the serpentine bands may have peaks and troughs and the first and second connectors may each extend from peaks of one of the serpentine bands to troughs of the adjacent serpentine band.

In some embodiments of the stent of this invention the first connector may have a first end and a second end such that the first end of the first connector may be circumferentially and longitudinally offset from the second end of the first connector and the second connector may have a first end and a second end such that the first end of the second connector may be circumferentially and longitudinally offset from the second end of the second connector.

In some embodiments of the stent of this invention the first connector may have a first end and a second end wherein the first end of the first connector and the second end of the first connector may be in axial alignment and the second connector may have a first end and a second end wherein the first end of the second connector and the second end of the second connector may be in axial alignment.

In some embodiments of the stent of this invention the length of the first connector may exceed the combined length of the two serpentine bands and the length of the second connector may exceed the combined length of the two serpentine bands.

In some embodiments the stent of this invention has serpentine bands such that each serpentine band has a magnitude. The magnitude may be the longitudinal distance from the proximal most portion of a serpentine band to the distal most portion of the same serpentine band. The connector may have a first end connected to a first serpentine band and a second end connected to a second serpentine band. The distance between the first and second ends of the connector may exceed the sum of the magnitudes of the two serpentine bands and the length of the second connector may exceed the sum of the magnitudes of the two serpentine bands.

In some embodiments the stent of this invention may comprise a first serpentine band and a second serpentine band wherein a first connector and a second connector may be circumferentially adjacent to the first connector. In some embodiments the first connector may have a curved portion of a first shape and the second connector may have a curved portion of a second shape wherein the first and second connectors may be cooperatively shaped so that the curved portion of the first connector may nest within the curved portion of the second connector.

In some embodiments the stent of this invention may comprise a plurality of the first connector and a plurality of the second connector wherein the first connectors and the second connectors may be arranged in pairs such that in each pair the curved portion of the first connector may nest within the curved portion of the second connector.

In some embodiments of the stent of this invention the first and second connectors may each be longer than the combined length of the first and second serpentine bands.

In some embodiments of the stent of this invention the first and second serpentine bands may each comprise peaks and troughs and the first and second connectors may each extend from a peak to a trough.

In some embodiments the stent of this invention may comprise a first segment and a second segment, an asymmetric first connector and an asymmetric second connector, and the first and second connectors may be constructed and arranged to nest with one another.

In some embodiments of the stent of this invention the first connector may have a first section of a first flexibility and a second section which may be more flexible than the first section and the second connector may have a first section of a first flexibility and a second section of a greater flexibility than the first section of the second connector wherein the second section of the first connector may nest within the first section of the second connector.

In some embodiments of the stent of this invention the shape of the second connector may correspond to the shape of the first connector rotated by 180 degrees.

In some embodiments of the stent of this invention the first and second segments may each be serpentine.

In some embodiments a stent may have two serpentine bands connected by at least three connectors including a first connector, a second connector, and a third connector. In at least one embodiment the first connector and the second connector each may have at least a first portion of a first curvature and a second portion of a second curvature wherein the second portion may be more flexible than the first portion. In at least one embodiment, the third connector may be disposed between the first connector and the second connector. In at least one embodiment, the second portion of the first connector may nest within a curved portion of the third connector and the said curved portion of the third connector may nest within the first portion of the second connector. In at least one embodiment, the second portion of the second connector may also nest within a curved portion of the third connector and said curved portion of the at least one third connector may nest within the first portion of the first connector.

Additional details and/or embodiments of the invention are discussed below.

DETAILED DESCRIPTION OF THE INVENTION

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, unless otherwise indicated, identical reference numerals used in different figures refer to the same component.

Figure 1:
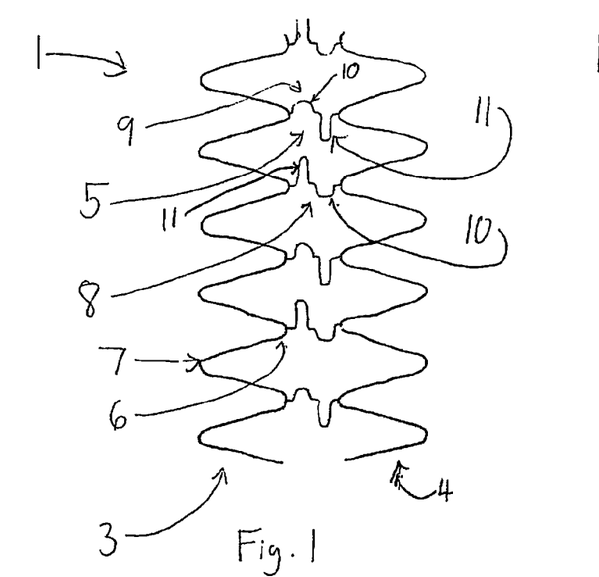
FIG. 1 is a flat pattern of an inventive stent in an as-cut configuration.

In one embodiment, the invention is directed to a stent such as that shown generally at 1 in FIG. 1. Stent 1 comprises at least one first serpentine band 3 and at least one second serpentine band 4 connected thereto. First serpentine band 3 and second serpentine band 4 include peaks 6 and troughs 7. For the purposes of this disclosure, "peak" shall refer to the portion of the serpentine bands (3,4) which are at the distal end of the band and "trough" shall refer to the portion of the serpentine bands (3,4) which are at the proximal end of the band; second serpentine band 4 is distal to first serpentine band 3.

Also, the term serpentine band includes within its scope bands that may be characterized as having one or more wavelengths as well as bands that are not characterizable as having a wavelength. The serpentine bands may be connected by at least two connectors including first connector 8 and second connector 9. The ends of each connector may be circumferentially aligned as shown in FIG. 1. The connectors 8 and 9 may each have a first portion 10 and a second portion 11. In some instances the second portion 11 may be more flexible than the first portion 10. The second portion 11 may be circumferentially longer than the first portion 10. The first portion 10 may be longitudinally longer than second portion 11. Stent 1 of FIG. 1 is shown with two serpentine bands for illustrative purposes only. The inventive stents of this disclosure may include three, four, five, six, seven or more bands. The number of bands will depend on the desired length of the stent and the length of each of the bands.

Figure 2:
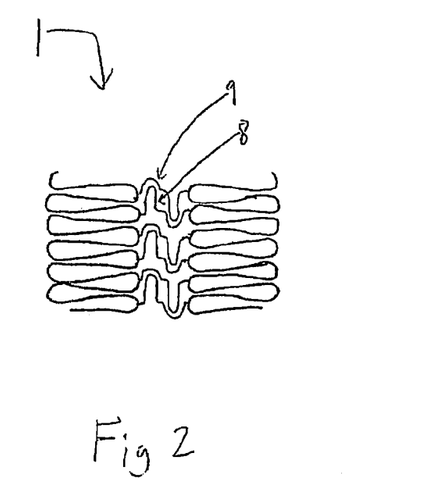
FIG. 2 is a flat pattern of the stent of FIG. 1 in a crimped configuration.

In at least one embodiment, when the inventive stent 1 is crimped onto a balloon or catheter the second portions 11 of the connectors nest into the first portions 10 of the connectors as shown in FIG. 2. Nesting typically allows for smaller crimped diameters because the limit of crimpability is dictated by the proximity of circumferentially adjacent peaks and circumferentially adjacent troughs rather than the proximity of circumferentially adjacent connectors. As illustrated in FIG. 2, the peaks 6 which are longitudinally aligned are in close proximity to the peaks immediately adjacent them and in some instances may actually touch one another.

Figure 3:
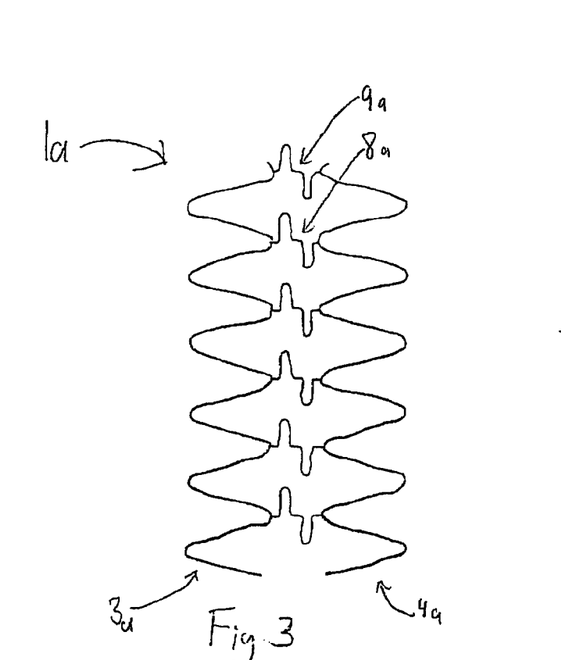
FIG. 3 is a flat pattern of a stent without connectors having nesting qualities.
Figure 4:
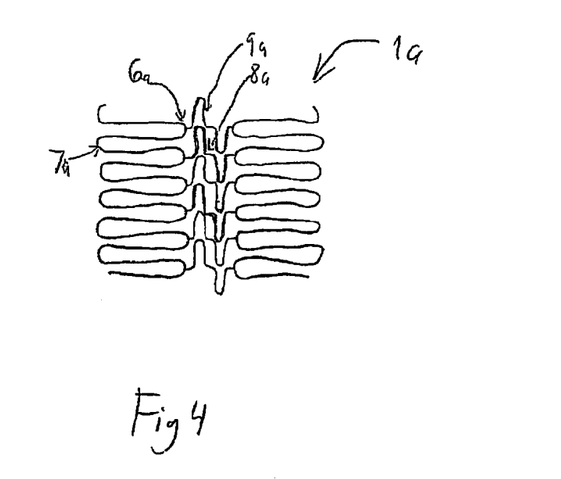
FIG. 4 is a flat pattern of the stent of FIG. 3 in a crimped configuration.

This is in contrast to the stent 1a of FIG. 3 which may have the same serpentine bands 3a, 4a as the serpentine bands 3, 4 of FIG. 1. However, the connectors 8, 9 of FIG. 3 are substantially identical, having substantially the same shape and orientation and do not nest when crimped as the stent 1 of FIG. 1 does. When the stent of FIG. 3 is crimped, as shown in FIG. 4, adjacent connectors contact one another before adjacent peaks contact one another and before adjacent troughs contact one another, thereby limiting the extent to which the stent may be crimped. Thus, the crimped stent of FIG. 4 has a larger diameter than the crimped stent 1 of FIG. 2.

Figure 5:
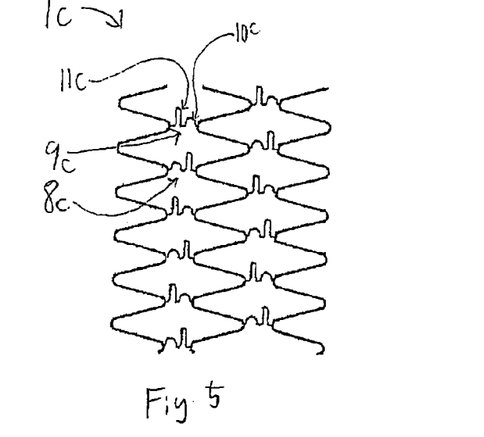
FIGS. 5-10 show other connectors that may be used in other embodiments of the inventive stents.

Another embodiment of the invention is shown in FIG. 5. The stent shown in FIG. 5 has 3 serpentine bands adjacent to one another and connected by connectors 8c and 9c. Each connector may have arcs in the first and second portions wherein each arc opens in the same circumferential direction. In this configuration the second portion 11c of each connector 8c does not reciprocally nest in a circumferentially adjacent connector 9c. Instead the second portion 11c of one connector nests in the first portion 11c of an adjacent connector whose second portion nests in another connector.

Figure 6:
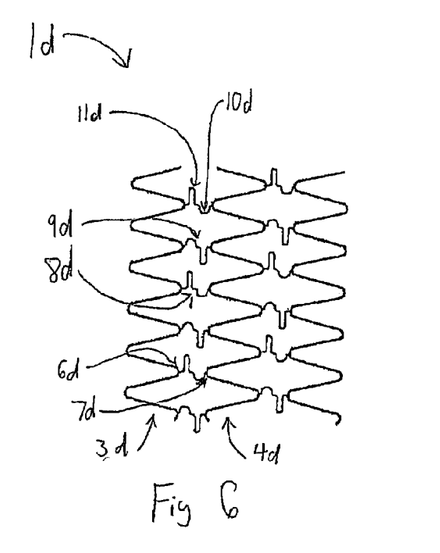

In at least one other embodiment of the invention, circumferentially adjacent arcs may open in alternating circumferential directions as shown in FIG. 6. In this configuration, circumferentially adjacent connectors may be paired in a nesting relationship. By way of example, connectors 9d and 8d may be paired up so as the second portions 1d of each connector reciprocally nest in the first portions of the connector it is paired with. In at least one embodiment, connectors 8d and 9d are related to one another by a rotation of 180 degrees. Thus, if connector 8d is rotated about its center by 180 degrees, the connector will be identical to 9d.

In at least one embodiment the ends of the connectors 9d, 8d are longitudinally aligned about a circumferential as shown in FIG. 6. In at least one embodiment, the serpentine bands are 180 degrees out of phase with one another in the circumferential direction. The connectors may connect at least one peak 6d of one serpentine band 3d to the closest trough 7d of a second serpentine band 4d as shown in FIG. 6. It should also be noted that the connectors may connect peaks to troughs that are not closest to them and/or which are circumferentially offset.

Figure 7:
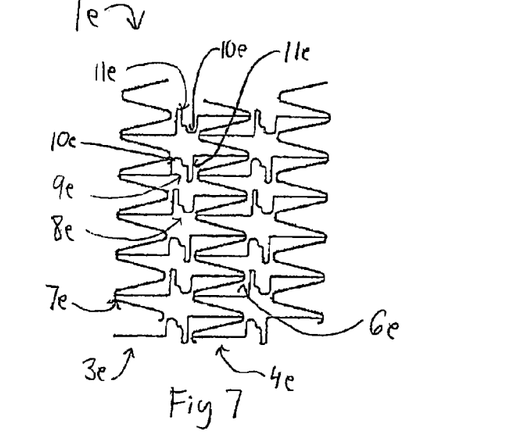

In the embodiment of FIG. 7, connectors 9e and 8e may be paired up so as the second portions 11e of each connector reciprocally nest in the first portions 10e of the connector it is paired with. In this configuration, each connector has ends which are circumferentially offset from one another. The connectors may connect at least one trough 7e of one serpentine band 3e with a peak 6e of a more distal serpentine band 4e.

In the embodiment of FIG. 7, serpentine band 3e is in phase circumferentially with serpentine band 4e.

Figure 8:
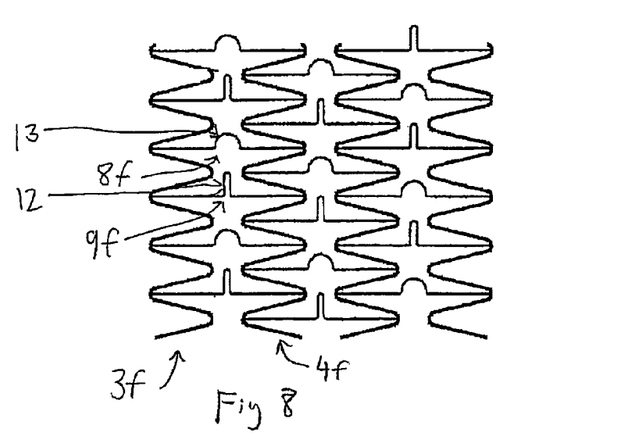

In at least one embodiment of the invention, as shown in FIG. 8, the stent may have serpentine bands 3f, 4f connected by connectors having a single arc. When crimped, the narrow arc 12 of connector 9f may nest within the broader arc 13 of connector 8f. It is noted, as shown in FIG. 8, that multiples of serpentine bands can be connected by the connectors shown in FIG. 8 as well as the connectors shown in FIGS. 5-7. The connectors may extend from a peak of serpentine band 3f to a peak, valley, or a region therebetween on serpentine band 4f. The connectors may also extend from a valley of serpentine band 3f to a peak, valley, or region therebetween on band 4f. In some embodiments the wider arc 13 is constructed of thinner and/or different material than the material constructing the more narrow arc. This may increases the flexibility of the wider arc 13 and may in some embodiments result in a flexibility similar to that of the more narrow arc 12. In some embodiments, this construction of the wider arc may also be applied to the connectors of FIGS. 5-7 with similar results.

Figure 9:
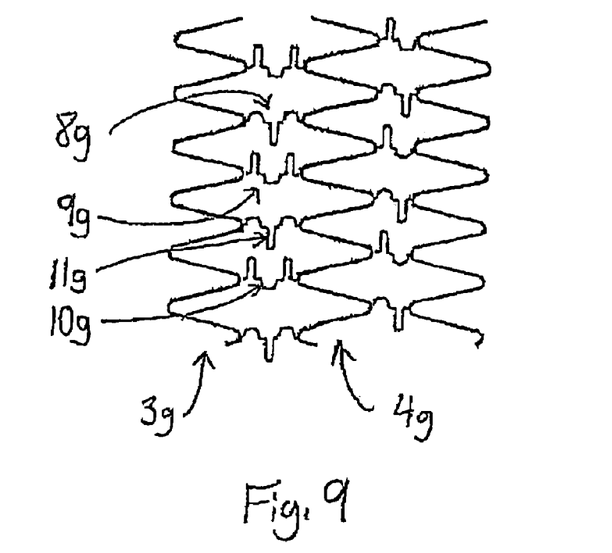

In at least one embodiment, connectors may include multiple first portions 10g and/or multiple second portions 11g as shown in FIG. 9. Connector 9g may have two second portions 11g which may nest within the two first portions 10g of connector 8g upon crimping the stent. In this configuration connectors 9g and 8g may be paired up so as the second portions 11g of each connector reciprocally nest in the first portions 10g of the connector it is paired with. In at least one embodiment, the orientation of the arcs of each connector may be similar to the arcs of FIG. 5 in that the arcs are in the same direction. In this configuration the second portions 11g of each connector 8g does not reciprocally nest in a circumferentially adjacent connector 9g. Instead, the second portions 11g of one connector nest in the first portions 10g of an adjacent connector whose second portion nests in another connector. In some embodiments, as shown in FIG. 9, some serpentine bands may be connected by connectors with more arcs than the connectors used in connecting other serpentine bands of the same stent.

Figure 10:
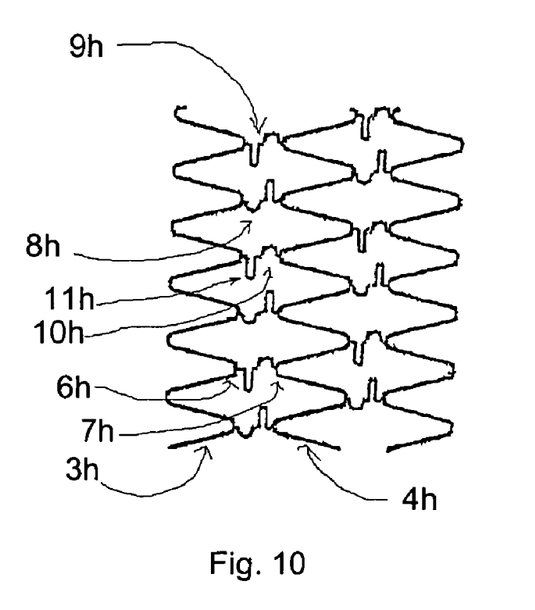

As shown in FIG. 10 the connectors 9h and 8h may nest in one another. In this embodiment one connector 8h with a second portion 11h more distal to a first portion 10h may have a second portion which extends as a circumferential peak which may nest within the first portion of an adjacent connector 9h. This may be considered to be in contrast to connectors 9d and 8d of FIG. 6 wherein one connector 9d with a second portion 11d more distal to a first portion 10d may have a second portion which extends as a circumferential valley which may nest within the first portion of an adjacent connector 9h.

Figure 11:
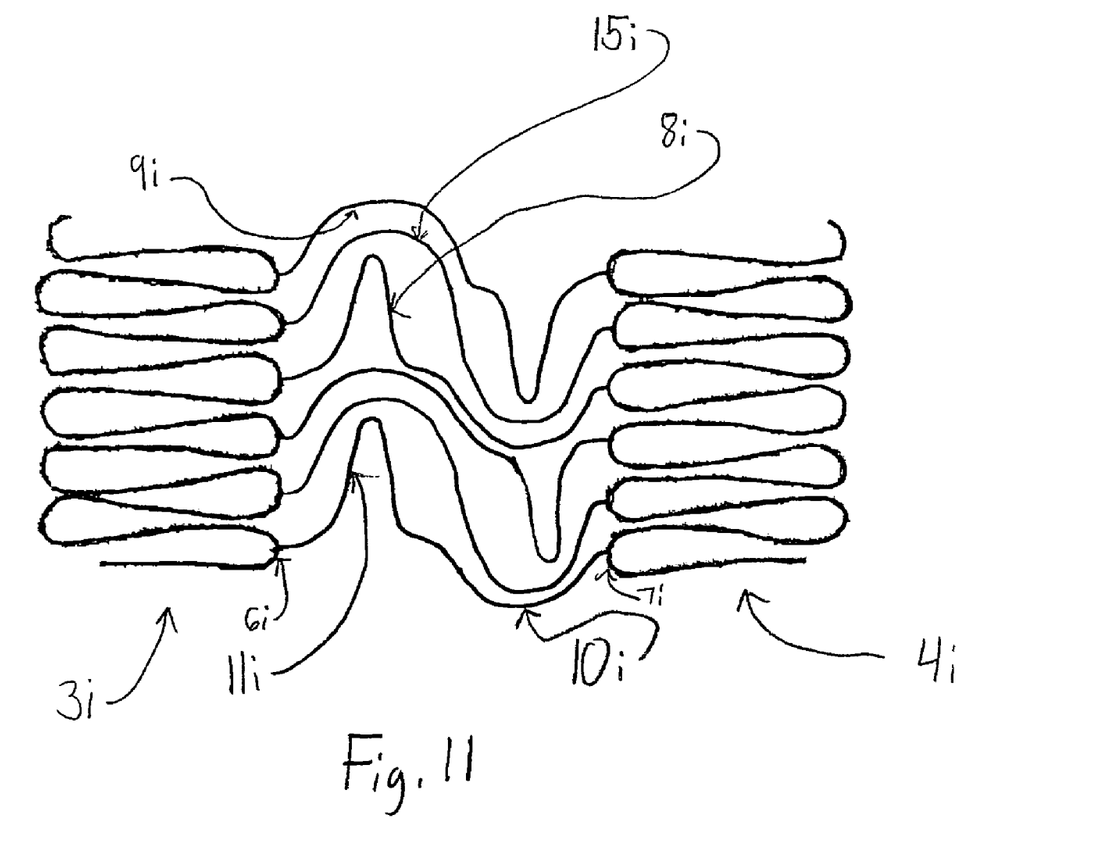
FIG. 11 is a flat pattern of an inventive stent of three different types of connectors which nest within each other.

As shown in FIG. 11, bands 3i and 4i are connected by at least 3 connectors which nest with one another. By way of example, connectors 9i, 8i, and 15i may be arranged together so as the second portions 11i of each connector nests within a curved portion of the middle connector 15i. The curved portions of middle connector 15i also nest within the first portions 10i of the connectors 9i and 8i which are both adjacent to middle connector 15i. It should be noted that the second portions 11i may nest within the curved portions of middle connector 15i such that the second portions 11i are in contact or are almost in contact with middle connector 15i. In at least one embodiment the middle connector 15i may also be in contact or almost in contact with the first portions 10i of connectors 9i and 8i. Middle connector 15i may have curved portions of various curvature. In at least one embodiment, connectors 8i and 9i are related to one another by a rotation of 180 degrees. Thus, if connector 8i is rotated about its center by 180 degrees, the connector may be substantially identical to 9i. In at least one embodiment, the second portion 11i of one connector 8i and the curved portion of a middle connector 15i both nest within the first portion 10i of connector 9i.

In at least one embodiment the ends of the connectors 9i, 8i, and 15i are longitudinally aligned about a circumferential as shown in FIG. 11. In at least one embodiment, the serpentine bands are 180 degrees out of phase with one another in the circumferential direction. The connectors may connect at least one peak 6i of one serpentine band 3i to the closest trough 7i of a second serpentine band 4i as shown in FIG. 11. It should also be noted that the connectors may connect peaks to troughs that are not closest to them and/or which are circumferentially offset.

The inventive stents disclosed herein may also be provided with adjacent serpentine bands having different phase relationships from those shown in the figures. For example, any of the stents disclosed herein may have adjacent serpentine bands which are 30, 45, 60, 90 or 120 degrees out of phase with one another. Any other phase relationship between adjacent bands is also within the scope of the invention. In the case where the serpentine bands are not characterizable as waves, adjacent serpentine bands may be identical to one another in shape and orientation or may differ from one another in shape and/or orientation.

Furthermore, it is also within the scope of the invention to modify where along the serpentine bands the connectors extend. For example, in any of the embodiments, the connectors may extend from peak to peak, from peak to trough, from peak to trough, from trough to peak, from a peak to a region between a peak and a trough, from a trough to a region between a peak and a trough or from a region between a peak and a trough to another region between a peak and a trough.

The inventive stent disclosed herein may be provided in embodiments in which the first and second serpentine band are characterized by the same total pathlength as each band is traversed about the circumference of the stent as well as in embodiments in which the pathlength of the first serpentine band is longer than or shorter than the pathlength of the second serpentine band as each band is traversed about the circumference of the stent.

Typically, the amplitude, pathlength, thickness, wavelength and width of the first and second serpentine bands will be chosen so that the radial strength of the first and second serpentine bands is identical. It is, however, within the scope of the invention for there to be differences in the radial strengths of the first and second serpentine bands. This could be achieved in a variety of ways including, for example, by maintaining the thickness and width of the first and second serpentine bands and by varying the length of the bands, by maintaining the length of the bands along with the thickness and varying the width of the bands, or by maintaining the length, thickness and width of the serpentine bands and varying the wavelength of the bands.

It is further within the scope of the invention for adjacent serpentine bands to be made of a different materials or of materials which are treated differently from one another so that adjacent bands of different wavelength and amplitude may have the same strength. Examples of different treatments include differently annealing some of the serpentine bands or subjecting some of the serpentine bands to a different heat treatment.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the serpentine bands and/or connectors may increase or decrease along portions of the stent or along the entire length of the stent. The amplitude and wavelength of several successive first serpentine bands may remain constant while the width and/or thickness of the successive first serpentine bands decreases. Similarly, the amplitude and wavelength of several successive second serpentine bands may remain constant while the width and/or thickness of the successive second serpentine bands decreases.

The flexibility of the inventive stents may be modified by varying the number of connectors between adjacent serpentine bands. For example, where more rigid ends are desired, the inventive stent may be provided with additional connectors extending between adjacent serpentine bands relative to the remainder of the stent. Where less rigid ends are desired, the number of connectors extending between adjacent serpentine bands may be decreased relative to the remainder of the stent.

The flexibility of the inventive stents may also be modified by varying the distance between adjacent serpentine bands. For example, where more rigid ends are desired, adjacent serpentine bands may be more closely spaced. Where less rigid ends are desired, adjacent serpentine bands may be spaced further apart.

The invention is also directed to a stent comprising a first serpentine band and a second serpentine band and an asymmetric first connector and an asymmetric second connector, where the first and second connectors are constructed and arranged to nest with one another. Examples of such a stent are shown in the figures discussed above. The individual serpentine bands of the figures discussed above do not include cells having fully enclosed openings. It is also within the scope of the invention to provide segments which include cells having fully enclosed openings. Examples of serpentine bands which would be suitable for use in the inventive stents include the bands disclosed in U.S. Pat. No. 6,231,598.

The invention is directed to any of the stents disclosed herein in an unexpanded state as well as in an expanded state, and in an as-cut state as well as a crimped state.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and welding the sheet, by electrode discharge machining, or by molding the stent with the desired design. The inventive stents may also be provided in the form of a coiled sheet.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys. such as stainless steel, tantalum and elgiloy. The invention also contemplates the use of more than one material in the inventive stents. For example, the first serpentine bands and the second serpentine bands may be made of different materials. Optionally, the connectors may be made of a different material than the first and/or second serpentine bands.

The inventive stents may be provided in mechanically expandable form, in self-expanding form or as a hybrid of the two. Mechanically expandable stents, in accordance with the invention, may be expanded using any suitable mechanical device including a balloon catheter.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers.

The inventive stents may find use in coronary arteries, renal arteries, peripheral arteries including illiac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate.

Suitable stent delivery devices including but not limited to those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may optionally be delivered in conjunction with one or more stent retaining sleeves. An example of stent retaining sleeves is disclosed in U.S. provisional application 60/238178. As such, the invention is also directed to a catheter with an inventive stent disposed thereabout.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims, each claim depending directly from claim 2 should be alternatively taken as depending from all previous claims, etc.). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 4 may be taken as alternatively dependent from claim 2; claim 5 may be taken as alternatively dependent from claim 1, 2 or 3, claim 6 may be taken as alternatively dependent from claims 2-4; etc.).

The invention claimed is:

1. A stent comprising: two serpentine bands; at least one first connector; and at least one second connector; the first and second connectors connecting the two serpentine bands together; the first connector and the second each having at least a first portion of a first curvature and a second portion of a second curvature, the second portion being more flexible than the first portion, wherein the first and second connector are adjacent one another and the second portion of the first connector nests within the first portion of the second connector and the second portion of the second connector nests within the first portion of the first connector wherein each serpentine band has a magnitude, the magnitude being the longitudinal distance from the proximal most portion of a serpentine band to the distal most portion of the same serpentine band, the connector having a first end connected to a first serpentine band and a second end connected to a second serpentine band, the distance between the first and second ends of the connector exceeding the sum of the magnitudes of the two serpentine bands and the length of the second connector exceeds the combined length of the magnitudes of the two serpentine bands.

2. The stent of claim 1 comprising a plurality of the first connectors and a plurality of the second connectors, the first and second connectors arranged in pairs, wherein in each pair, the second portion of one first connector nests within the first portion of one second connector and the second portion of one second connector nests within the first portion of one first connector.

3. The stent of claim 2 comprising a plurality of the serpentine bands, wherein adjacent serpentine bands are connected by a plurality of the first connector and a plurality of the second connector, wherein first and second connectors which are circumferentially adjacent one another are arranged in pairs, wherein in each pair, the second portion of one first connector nests within the first portion of one second connector and the second portion of one second connector nests within the first portion of one first connector.

4. The stent of claim 1 wherein each first connector includes at least one linear section connecting the first and second portions of the first connector and each second connector includes at least one linear section connecting the first and second portions of the second connector.

5. The stent of claim 1 wherein the second connector has a shape which corresponds substantially to that of the first connector, rotated by 180 degrees.

6. The stent of claim 1 crimped about a catheter.

7. The stent of claim 1 wherein the first portion of the first connector has a greater width than the second portion of the first connector and the first portion of the second connector has a greater width than the second portion of the second connector.

8. The stent of claim 1 wherein the first portion of the first connector has a greater thickness than the second portion of the first connector and first portion of the second connector has a greater thickness than the second portion of the second connector.

9. The stent of claim 1 wherein the serpentine bands have peaks and troughs and the first and second connectors each extend from peaks of one of the serpentine bands to troughs of the adjacent serpentine band.

10. The stent of claim 1 wherein the first end of the first connector circumferentially and longitudinally offset from the second end of the first connector and the first end of the second connector circumferentially and longitudinally offset from the second end of the second connector.

11. The stent of claim 1 wherein the first end of the first connector and the second end of the first connector in axial alignment and the first end of the second connector and the second end of the second connector in axial alignment.

12. The stent of claim 1 wherein the first connector has a first section of a first flexibility and a second section which is more flexible than the first section, and the second connector has a first section of a first flexibility and a second section of a greater flexibility than the second section of the second connector, wherein the first section of the first connector nests within the second section of the second connector.

13. The stent of claim 1 wherein the shape of the second connector corresponds to the shape of the first connector rotated by 180 degrees.

* * * * *